United States Patent [19]

Peterson

[11] Patent Number: 5,003,635

[45] Date of Patent: Apr. 2, 1991

[54] CLOTHING INCLUDING INSECT REPELLENT STRIPS

[76] Inventor: James H. Peterson, 1951 Montview Dr., Greeley, Colo. 80631

[21] Appl. No.: 404,210

[22] Filed: Sep. 7, 1989

[51] Int. Cl.⁵ .......................... A41D 13/00; A42B 1/00
[52] U.S. Cl. .......................................... 2/69; 2/171.2; 2/170; 2/2; 2/4; 2/DIG. 11; 2/174; 428/138; 428/40; 36/1; 36/98
[58] Field of Search ...................... 2/69, 171.2, 170, 2, 2/4, DIG. 11, 174; 428/138, 40; 36/1, 98

[56] References Cited

U.S. PATENT DOCUMENTS

| | | | |
|---|---|---|---|
| 3,567,119 | 3/1971 | Wilbert et al. | 2/171.2 |
| 3,767,785 | 10/1973 | Bordenca | 2/171.2 |
| 4,186,502 | 2/1980 | Foster | 36/1 |
| 4,277,024 | 7/1981 | Spector | 428/40 |

FOREIGN PATENT DOCUMENTS 1036301  8/1978  Canada .......................................... 2/4

Primary Examiner—Werner H. Schroeder
Assistant Examiner—Gloria Hale
Attorney, Agent, or Firm—Dean P. Edmundson

[57] ABSTRACT

Systems and techniques are described for providing insect repellent characteristics to a wide variety of wearing apparel. Elongated flexible insect repellent strips are secured to or retained in cavities in various articles of apparel to repel insects from the person wearing such apparel. The systems and techniques are applicable to all types of wearing apparel such as stockings, shoes, trousers, hats, shirts, etc.

11 Claims, 5 Drawing Sheets

FIG. 1
FIG. 1A
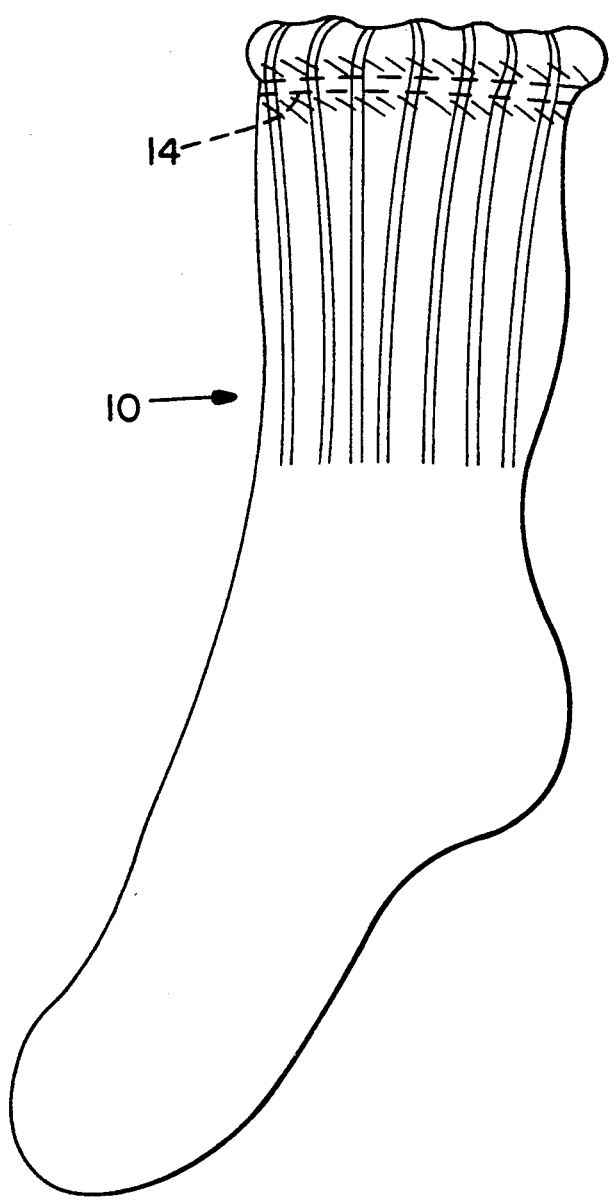
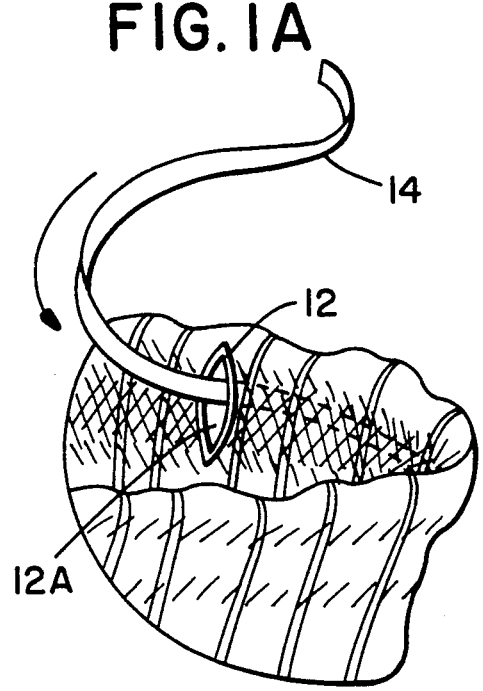

FIG. 2
FIG. 2A
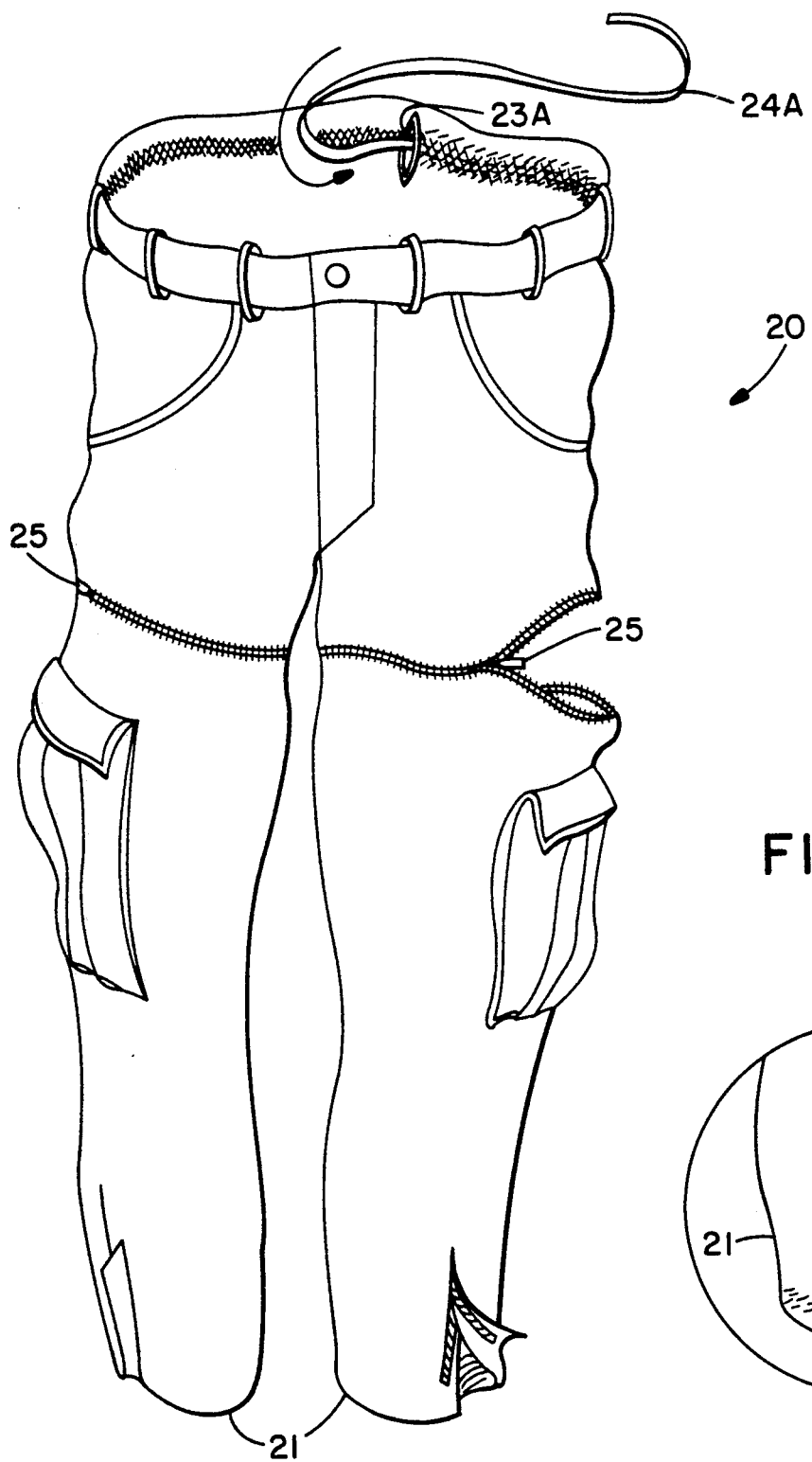
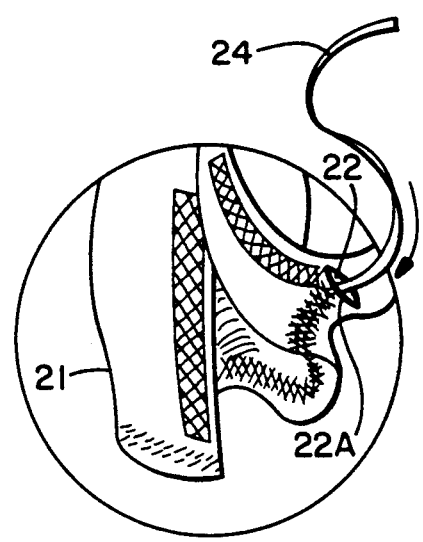

CLOTHING INCLUDING INSECT REPELLENT STRIPS

FIELD OF THE INVENTION

This invention relates to clothing. In another aspect this invention relates to outdoor clothing and means for repelling insects. More particularly, this invention relates to clothing intended for outdoor use and which includes means for repelling insects.

BACKGROUND OF THE INVENTION

The problem of tick-borne diseases such as Rocky Mountain spotted fever and lyme disease as well as other insect-borne disorders such as plague and typhus endanger, or at least encumber, biologists and field workers as well as a growing number of nature enthusiasts.

Although there are a variety of commercially-available insect repellents which are used by both children and adults, such repellents have various disadvantages. For example, there are a number of commercially-available repellent sprays, lotions and powders which have been sold for many years. However, use of such repellent materials is cumbersome and inconvenient. Also, such materials are often greasy and emit unpleasant odors. Many people are sensitive to the odors of these materials. Such materials can also stain certain types of clothing.

Further, convenient insect repellent materials can be difficult or inconvenient to apply to the desired areas in a uniform and effective manner. Also, perspiration can cause dilution of such materials which thereby results in diminished effectiveness. Furthermore, conventional insect repellent sprays, lotions, etc. must be periodically re-applied throughout the day.

There has not heretofore been provided a safe, effective, and easy-to-use insect repellent system for use by humans which avoids the problems inherent with the use of prior insect repellents.

SUMMARY OF THE PRESENT INVENTION

In accordance with the present invention there are provided techniques and systems for rendering clothing (i.e., all types of wearing apparel) repellent to insects.

In a preferred embodiment an article of outdoor clothing is provided with an annular cavity into which there is placed an elongated flexible insect repellent strip to repel insects such as ticks and fleas and prevent such insects from locating on the human body. The cavity preferably extends entirely around the portion of the body covered by the article of clothing. This is referred to herein as an annular cavity. For example, when the article is a stocking, preferably the cavity extends completely around the lower portion of the leg of the person wearing the stocking.

The systems and techniques of the invention are much more convenient and effective than conventional sprays, lotions, powders, etc. Also, the systems of this invention do not stain the clothing and they are not diluted by perspiration.

Thus, the invention provides a line of outdoor clothing which includes cavities or pockets for the insertion of repellent impregnated plastic strips at vulnerable insect entry points such as ankles, collars, belt lines, headbands, sleeves, etc.

Other advantages of the systems and techniques will become apparent from the following detailed description and the accompanying drawings.

BRIEF DESCRIPTION OF THE DRAWINGS

The invention is described in more detail hereinafter with reference to the accompanying drawings, wherein like reference characters refer to the same parts throughout the several views and in which:

FIG. 1 is a side elevational view of one embodiment of wearing apparel of the invention which includes an insect repellent strip;

FIG. 1A illustrates one manner in which an insect repellent strip is inserted into a cavity in the article of FIG. 1;

FIG. 2 is a perspective view of another embodiment of wearing apparel of the invention;

FIG. 2A illustrates one manner in which an insect repellent strip is inserted into a cavity at the lower end of one of the legs of the trousers of FIG. 2;

DETAILED DESCRIPTION OF THE INVENTION

Figure 3:
FIG. 3 is a perspective view of another embodiment of wearing apparel of the invention.

In FIGS. 1 and 1A there is illustrated one embodiment of wearing apparel, a stocking 10, which includes an annular cavity 12 adjacent to the opening at the top of the stocking. In other words, the cavity extends all the way around the interior circumference of the open end of the stocking. The cavity may be made from nylon mesh or other porous fabric, for example.

An elongated flexible insect repellent strip 14 is inserted into cavity 12 through opening 12A, as indicated by the arrow. The strip 14 is retained and carried within the cavity.

The upper portion of the stocking includes conventional elastic so that the upper portion of the stocking will conform to the leg of the person wearing the stocking. This also causes the strip 14 to be closely disposed next to the skin of the wearer during use to repel insects and prevent them from advancing up the leg.

FIGS. 2 and 2A illustrate another embodiment of the invention. In this example the wearing apparel comprises trousers 20 having lower leg portions 21. Each lower leg portion includes a cavity 22 which is annular (i.e., the cavity extends completely or substantially completely around the circumference of the lower leg portion of the trousers). Inserted into the cavity through opening 22A is an elongated flexible insect repellent strip 24. These strips prevent ticks, fleas, and other such insects from entering the lower open ends of the legs of the trousers.

At the upper end of the trousers, i.e., at the waist portion, there is another cavity which extends completely or substantially completely around the waist portion of the trousers. An elongated flexible insect repellent strip 24A is inserted into this cavity through opening 23A. This strip prevents insects from entering into the trousers at the waist.

This particular pair of trousers includes zipper means 25 for detachably fastening the lower leg portions 21 to the upper portion of the trousers.

FIG. 3 illustrates another embodiment of wearing apparel which includes the insect repellent system in accordance with the present invention. This embodiment comprises a shoe or boot 30. The upper open portion thereof includes an annular cavity (having opening 32A) which extends completely or substantially completely around the opening of the shoe or boot.

An elongated flexible insect repellent strip 34 is located with the cavity after being inserted through opening 32A.

Figure 4:
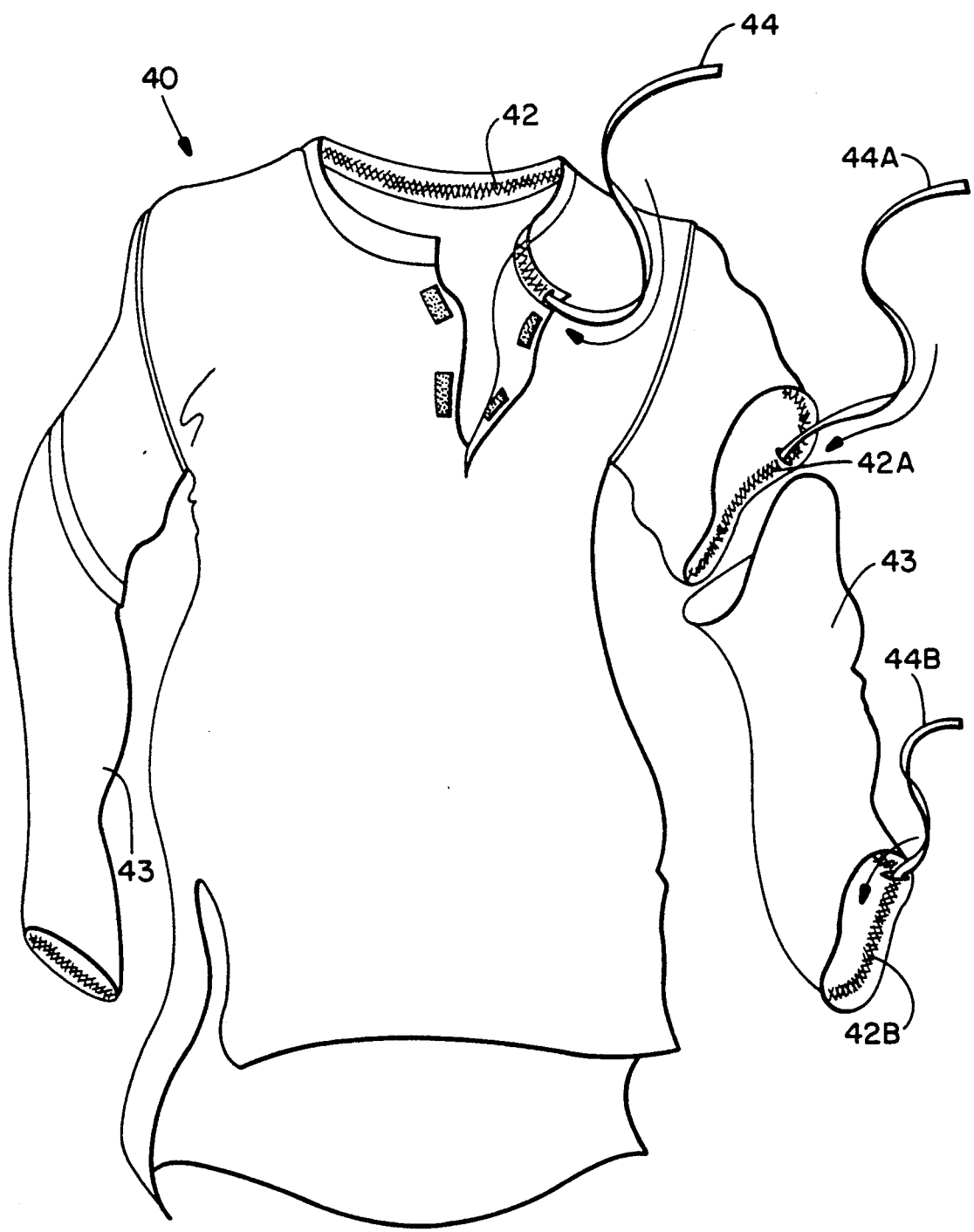
FIG. 4 is a perspective view of another embodiment of wearing apparel of the invention.

FIG. 4 illustrates yet another embodiment of wearing apparel of this invention. This embodiment comprises a shirt 40 having an open neck portion which includes cavity 42 extending around the neck portion. An elongated flexible insect repellent strip 44 is inserted into this cavity and, when the neck portion is closed, the insect repellent strip extends around the neck of the wearer.

The shirt 40 also includes a cavity 42A extending around the arm portion at a point downward from the shoulder but above the elbow. Another elongated insect repellent strip 44A is inserted into this cavity.

The lower end of each sleeve 43 also includes a cavity 42B extending around it. An elongated flexible insect repellent strip 44B is inserted into this cavity.

With the separate insect repellent strips at the various locations in the shirt, there is very good protection provided to prevent insects from entering into the shirt.

Figure 5:
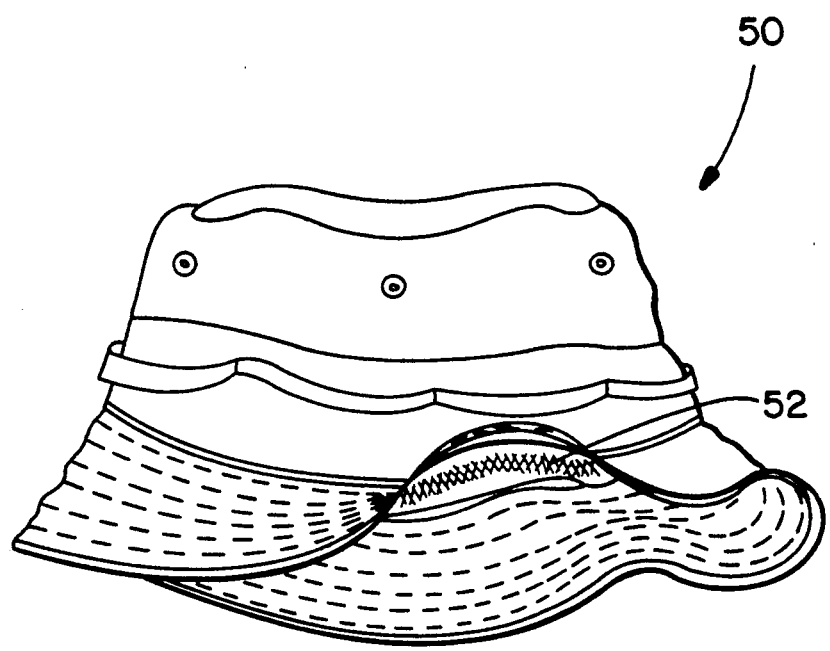
FIGS. 5 and 6 are illustrate other embodiments of wearing apparel of the invention including insect repellent strips.

FIG. 5 illustrates another embodiment of wearing apparel which includes the insect repellent strip system of this invention. This embodiment comprises a hat 50 which includes an annular cavity 52 extending completely or substantially completely around the inside of the hat. Inside the cavity there is provided an elongated flexible insect repellent strip of the type illustrated and described above in connection with the other embodiments.

Figure 6:
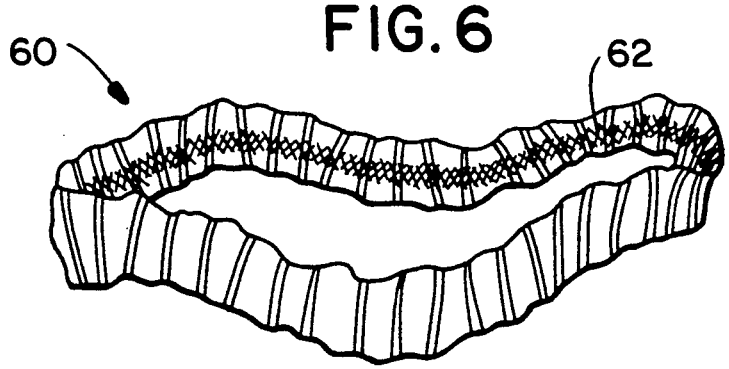

FIG. 6 illustrates a headband 60 which includes an annular cavity 62 which extends around the inside of the band. An elongated flexible insect repellent strip of the type illustrated and described above is contained within the cavity.

The band 60 could be provided in any desired size and accordingly may be worn on an arm or leg, if desired, to provide protection against insects. More than one band may be worn on each limb, if desired.

Thus, the insect repellent system of this invention is easily incorporated into field clothing or other such wearing apparel. The system is safe, convenient, and effective. The system is applicable not only to consumer use by also for military use.

The type of insect repellent strips used in this invention may vary. When a strip is no longer effective it can be easily taken out and replaced with a fresh strip. The insect repelling compounds(s) used may vary, as desired. Preferably the compound(s) is impregnated in plastic or the like in a manner such that it will diffuse at a rate sufficient to repel all insects.

Other variants are possible without departing from the scope of this invention.

What is claimed is:

1. An article of clothing to be worn on the human body including a flexible insect-repellent strip which is adapted to conform to the portion of said body covered by said article; wherein said article comprises a stocking having an elastic upper portion, and wherein said flexible strip is carried by said upper portion.

2. An article in accordance with claim 1, wherein said article includes an annular cavity, and wherein said flexible strip is contained within said cavity.

3. A system for repelling insects, said system comprising an article of clothing to be worn on the human body, said article including an annular cavity, and further comprising an elongated flexible insect-repellent strip retained within said cavity; wherein said article comprises trousers.

4. A method for repelling insects from the human body comprising:
    (a) providing an article of clothing including an annular cavity therein; wherein said article comprises a stocking;
    (b) providing an elongated flexible insect-repellent strip;
    (c) inserting said insect-repellent strip into said cavity; and
    (d) applying said article of clothing onto said body.

5. An article of clothing to be worm on the human body including a flexible insect-repellent strip which is adapted to conform to the portion of said body covered by said article; wherein said article includes an annular cavity and said flexible strip is contained with said cavity; wherein said article comprises as shoe having an ankle-encircling portion, and wherein said cavity is located in said ankle-encircling portion.

6. A system for repelling insects, said system comprising an article of clothing to be worm on the human body, said article including an annular cavity, and further comprising an elongated flexible insect-repellent strip retained within said cavity; wherein said article comprises a shirt.

7. A system for repelling insects, said system comprising an article of clothing to be worn on the human body, said article including an annular cavity, and further comprising an elongated flexible insect-repellent strip retained within said cavity; wherein said article comprises a hat.

8. A system in accordance with claim 3, wherein said trousers have an open waist portion and two leg members including open lower ends; wherein each said end includes a said annular cavity; and wherein each said cavity includes a said flexible strip.

9. A system in accordance with claim 8, wherein said waist portion includes an annular cavity, and wherein a said flexible repellent strip is contained in said cavity.

10. A system in accordance with claim 6, wherein said shirt includes an open neck portion and long sleeve members including wrist-encircling portions; and wherein each said sleeve member includes a said cavity and a said flexible strip member.

11. A system in accordance with claim 10, wherein said neck portion includes a said cavity and a said flexible strip member.

* * * * *